United States Patent [19]

Böger et al.

[11] Patent Number: 4,511,571
[45] Date of Patent: Apr. 16, 1985

[54] N-(2-PYRIDYLOXYPHENYL)-N'-BENZOYL UREAS, PESTICIDAL COMPOSITIONS CONTAINING SAME AND PESTICIDAL METHODS OF USE

[75] Inventors: Manfred Böger, Weil am Rhein, Fed. Rep. of Germany; Josef Ehrenfreund, Allschwil, Switzerland; Pierre Martin, Rheinfelden, Switzerland; Eginhard Steiner, Füllinsdorf, Switzerland

[73] Assignee: Ciba Geigy Corporation, Ardsley, N.Y.

[21] Appl. No.: 433,763

[22] Filed: Oct. 12, 1982

[30] Foreign Application Priority Data

Oct. 20, 1981 [CH] Switzerland .................. 6691/81
May 26, 1982 [CH] Switzerland .................. 3231/82
Sep. 3, 1982 [CH] Switzerland .................. 5248/82

[51] Int. Cl.³ .................. C07D 213/64; A01N 43/40
[52] U.S. Cl. .................. 514/351; 546/291
[58] Field of Search .................. 546/291; 424/263

[56] References Cited

U.S. PATENT DOCUMENTS 4,003,763  1/1977  Johnston .................. 71/94
4,173,637 11/1979  Nishiyama et al. .................. 424/263

FOREIGN PATENT DOCUMENTS 0028870  5/1981  European Pat. Off. .................. 546/302

Primary Examiner—Alan L. Rotman
Attorney, Agent, or Firm—Frederick H. Rabin; Bruce M. Collins

[57] ABSTRACT

Novel substituted N-(2-pyridyloxyphenyl)-N'-benzoylureas of the formula

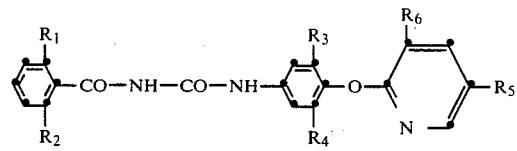

wherein
$R_1$, $R_2$, $R_3$ and $R_4$ independently of one another are each hydrogen, methyl or halogen,
$R_5$ is the radical $-CHF_2$, or a $C_2$–$C_{10}$-alkyl group which is uniformly or nonuniformly substituted by 1 to 21 halogen atoms, and
$R_6$ is halogen, processes and starting products for producing these compounds, as well as compositions containing these, for use in combating pests, particularly for combating insects which infest plants and animals. The novel compounds have a specially high ovolarvicidal and ovicidal action against insects that damage plants.

16 Claims, No Drawings

N-(2-PYRIDYLOXYPHENYL)-N'-BENZOYL UREAS, PESTICIDAL COMPOSITIONS CONTAINING SAME AND PESTICIDAL METHODS OF USE

The present invention relates to novel substituted N-(2-pyridyloxyphenyl)-N'-benzoylureas, to processes for producing them, and to their use for combating pests. The invention relates also to novel intermediates suitable for producing these compounds, and no processes for obtaining the intermediates.

The substituted N-(2-pyridyloxyphenyl)-N'-benzoylureas according to the invention have the formula I

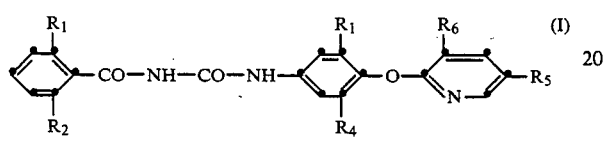

wherein $R_1$, $R_2$, $R_3$ and $R_4$ independently of one another are each hydrogen, methyl or halogen, $R_5$ is the radical —$CHF_2$, or a $C_2$–$C_{10}$-alkyl group which is uniformly or nonuniformly substituted by 1 to 21 halogen atoms, and $R_6$ is halogen.

Halogen within the scope of the present invention is preferably fluorine, chlorine or bromine, particularly fluorine or chlorine.

Compounds of the formula I preferred on account of their action as pesticidal active substances are those wherein $R_5$ is the radical —$CHF_2$, or an ethyl group which is uniformly or nonuniformly substituted by 1 to 5 fluorine or chlorine atoms; in particular it is a radical from the group comprising: —$CH_2$—$CF_3$, —$CF_2$—$CF_2Cl$, —$CF_2$—$CFCl_2$, —$CCl_2$—$CCl_3$, —$CF_2$—$CCl_3$, —$CF_2$—$CH_3$, —$CCl_2$—$CH_3$, —$CF_2$—$CF_3$, —$CH_2$—$CH_2Cl$, —$CH_2$—$CHCl_2$ and —$CH_2$—$CCl_3$. Further valuable compounds of the formula I by virtue of their biological activity are those wherein $R_3$ and $R_4$ independently of one another are each hydrogen, methyl or chlorine. To be emphasised in particular are compounds of the formula I wherein $R_6$ is chlorine.

The compounds of the formula I can be produced by processes known per se (cp., inter alia, the German Offenlegungsschriften Nos. 2,123,236, 2,601,780 and 2,748,636).

Thus, for example, a compound of the formula I can be obtained (a) by reaction of a compound of the formula II

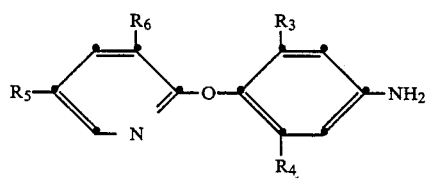

with a compound of the formula III

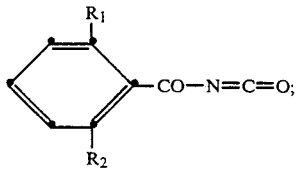

or (b) by reaction of a compound of the formula IV

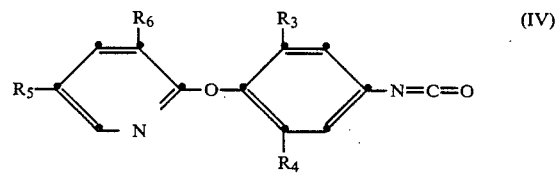

with a compound of the formula V

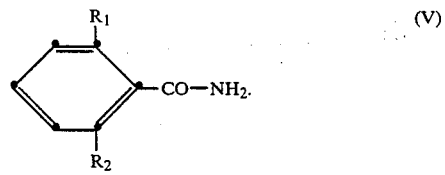

In the above formulae II, III, IV and V, the symbols $R_1$, $R_2$, $R_3$, $R_4$, $R_5$ and $R_6$ have the meanings defined under the formula I.

The processes (a) and (b) mentioned are preferably performed under normal pressure and in the presence of an organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, especially benzene, toluene, xylene, chloroform, methylene chloride, carbon tetrachloride and chlorobenzene; nitriles, such as acetonitrile or propionitrile; dimethyl sulfoxide, as well as ketones, for example acetone, methyl ethyl ketone, methylisopropyl ketone and methylisobutyl ketone. Process (a) is in general performed at a temperature of −10° to 100° C., preferably between 15° and 40° C., optionally in the presence of an organic base, for example triethylamine. Process (b) is carried out at a temperature of 0° to 120° C., preferably at the boiling point of the employed solvent, and optionally in the presence of an organic base, such as pyridine, and/or with the addition of an alkali metal or alkaline-earth metal, preferably sodium.

The p-pyridyloxyanilines of the formula II and the p-pyridyloxyphenylisocyanates of the formula IV are novel compounds. These compounds and the production thereof likewise from subject matter of the present invention. The compounds of the formula II can be obtained, using one of the customary processes [cp. for example: Rec. 21, 271 (1902); J. Am. Soc. 68, 1604 (1964); J. Org. Chem. 11, 378 (1946); and Rec. 79, 995 (1970)], by reaction of correspondingly substituted p-nitrophenols of the formula VI with corresponding reactive pyridines of the formula VII, and subsequent reduction of the nitro group in the formed compounds of the formula VIII:

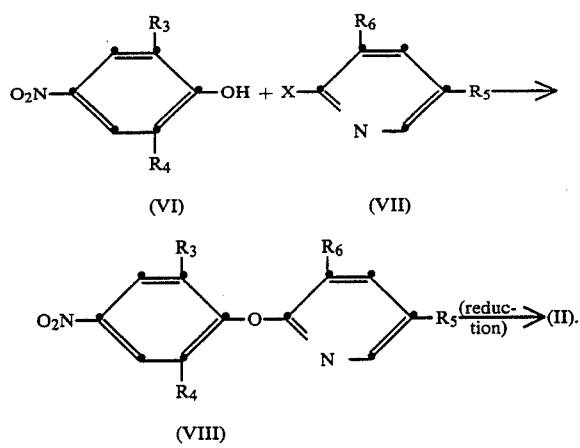

In the above formulae VI to VIII, the symbols $R_3$ to $R_6$ have the meanings defined in the foregoing under the formula I, and X is halogen, preferably chlorine.

The substituted pyridines of the formula VII are also novel compounds, which can be obtained, by means of a ring-closure reaction, by reaction of acrylonitrile with an aldehyde of the formula $R_5$—$CCl_2$—CH=O, optionally with isolation of an intermediate of the formula N≡C—CHCl—$CH_2$—CCl($R_5$)—CH=O, and preferably in the presence of a hydrogen halide HX, wherein X is fluorine, chlorine or bromine, and $R_5$ has the meaning defined under the formula I. A resulting compound of the formula VII can be modified by further halogenation or halogen exchange in the group $R_5$ within the aforementioned meaning defined under the formula I.

The pyridyloxyphenylisocyanates of the formula IV are obtainable by reaction of the correspondingly substituted anilines of the formula II with phosgene, using in general customary processes.

The starting materials of the formulae III and V given in the foregoing are known, and can be produced by processes analogous to known processes. The compounds of the formula III can thus be obtained as follows (cp. J. Agr. Food Chem. 21(3), 348 and 993, 1973):

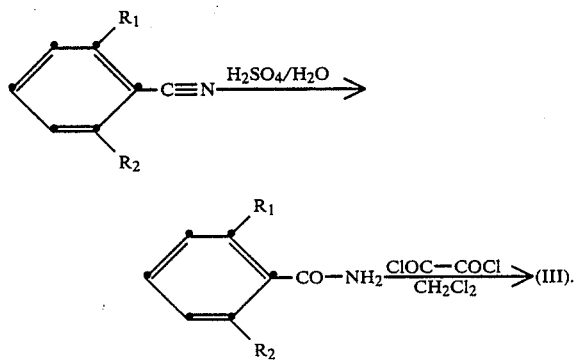

In the above formulae, $R_1$ and $R_2$ have the meanings given under the formula I.

It is known that specific N-phenyl-N'-benzoylureas have insecticidal properties (cp. European Patent Application No. 0016729, German Offenlegungsschriften Nos. 2,123,236, 2,504,982, 2,537,413, 2,601,780 and 2,726,684, the Belgian Patent Specifications Nos. 832,304, 843,906, 844,066 and 867,046, and also the U.S. Pat. No. 4,089,975). From the German Offenlegungsschrift No. 2,748,636 are already known substituted N-(trifluoromethylpyridyloxy)-phenyl-N'-benzoylureas which have insecticidal properties.

It has now been found that surprisingly, compared with the above compounds, the compounds of the formula I according to the invention, whilst having a high tolerance to plants and negligible toxicity to warm-blooded animals, exhibit an excellent degree of effectiveness as pesticidally active substances. They are suitable in particular for combating pests which infest plants and animals.

The compounds of the formula I are especially suitable for combating insects of the orders: Lepidoptera, Coleoptera, Homoptera, Heteroptera, Diptera, Thyanoptera, Orthoptera, Anoplura, Siphonaptera, Mallophaga, Thysanura, Isoptera, Psocoptera and Hymenoptera.

The good insecticidal action of the compounds of the formula I according to the invention corresponds to a mortality rate of at least 50–60% of the harmful insects mentioned.

Besides having a very favourable action against flies, for example *Musca domestica*, and against mosquito larvae, compounds of the formula I are suitable also for combating insects which damage plants by eating, in crops of ornamental plants and productive plants, especially in cotton crops (for example against *Spodoptera littoralis* and *Heliothis virescens*), and also in vegetable crops (for example against *Leptinotarsa decemlineata* and *Pieris brassicae*). To be emphasised in particular is the ovicidal and larvicidal action of compounds of the formula I. When compounds of the formula I are taken up with the feed by adult insects, there is observed in many cases, especially with Coleoptera, for example *Anthonomus grandis*, a reduced oviposition and/or a lessened rate of hatching.

The compounds of the formula I are moreover suitable for combating ectoparasites in both domestic and productive animals, for example by treatment of animals, livestock housing and pasture land.

The action of the compounds according to the invention or of the compositions containing them can be considerably broadened and adapted to suit prevailing conditions by the addition of other insecticides and/or acaricides.

The compounds of the formula I are used either in an unmodified form or preferably together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objectives to be achieved and the given conditions.

The formulation, that is to say, the compositions or preparations containing the active ingredient of the formula I, or combinations of this active ingredient with other insecticides or acaricides, and optionally a solid or liquid additive, are produced in a known manner, for example by the intimate mixing and/or grinding of the active substance with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalates, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acids or highly dispersed absorbent polymers. Suitable granulated adsorptive carriers are porous types, for example pumice, ground brick, sepiolite or bentonite; and suitable nonsorbent carriers are materials such as calcite or sand. A great number of pre-granulated materials of inorganic or organic nature, such as in particular dolomite or ground plant residues, can also be used.

Suitable surface-active compounds are, depending on the nature or the active ingredient of the formula I, or of the combinations of this active ingredient with other insecticides or acaricides, to be formulated, nonionic, cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$–$C_{22}$), for example the sodium or potassium salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and they generally contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are the salts or sulfuric acid esters and sulfonic acids of fatty alcohol ethylene oxide adducts. The sulfonated benzimidazole derivatives preferably contain 2 sulfonic acid groups and a fatty acid group having about 8-22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethyl ammonium chloride or benzyldi-(2-chloroethyl)-ethylammonium bromide.

The tensides customarily used in formulation practice are described, inter alia, in the following publications:

"Mc Cutcheon's Detergents and Emulsifiers Annual", MC Publishing Corp., Ringwood, N.J., 1979, and Sisely and Wood, "Encyclopedia of Surface Active Agents", Chemical Publishing Co., Inc. New York (1979).

The pesticidal preparations contain as a rule 0.1 to 99%, particularly 0.1 to 95%, of active ingredient of the formula I, or of combinations of this active ingredient with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule preparations having considerably lower concentrations of active ingredient.

The compositions can also contain additives, such as stabilisers, antifoaming agents, viscosity regulators, binders and adhesives, as well as fertilisers or other active substances for obtaining special effects.

| Formulation examples for liquid active ingredients of the formula I or combinations of these active ingredients with other insecticides or acaricides (% = per cent by weight) | | | |
| --- | --- | --- | --- |
| 1. Emulsion concentrates | (a) | (b) | (c) |
| active ingredient or active ingredient combination | 25% | 40% | 50% |
| calcium dodecylbenzenesulfonate | 5% | 8% | 6% |
| castor-oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2. Solutions | (a) | (b) | (c) | (d) |
|---|---|---|---|---|
| active ingredient or active-ingredient combination | 80% | 10% | 5% | 95% |
| ethylene glycol-monomethyl ether | 20% | — | — | — |
| polyethylene glycol MG 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active ingredient or active-ingredient combination | 5% | 10% |
| kaolin | 94% | — |
| highly dispersed silicic acid | 1% | — |
| attapulgite | — | 90% |

The active ingredient is dissolved in methylene chloride; the solution is then sprayed onto the carrier, and the solvent is subsequently evaporated of in vacuo.

| 4. Dusts | (a) | (b) |
|---|---|---|
| active ingredient or active-ingredient combination | 2% | 5% |
| highly dispersed silicic acid | 1% | 5% |
| talcum | 97% | — |
| kaolin | — | 90% |

Ready-for-use dusts are obtained by the intimate mixing of the carriers with the active ingredients.

Formulation examples for solid active ingredients of the formula I or combination of these active ingredients with other insecticides or acaricides (% = percent by weight)

| 5. Wettable powders | (a) | (b) | (c) |
|---|---|---|---|
| active ingredient or active-ingredient combination | 25% | 50% | 75% |
| sodium lignin sulfonate | 5% | 5% | — |
| sodium lauryl sulfate | 3% | — | 5% |
| sodium diisobutylnaphthalenesulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient or the active-ingredient combination is well mixed with the additives, and the mixture is thoroughly ground in a suitable mill. Wettable powders which can be diluted with water to give suspensions of the required concentration are obtained.

| 6. Emulsion concentrate | |
|---|---|
| active ingredient or active-ingredient combination | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| 7. Dusts | (a) | (b) |
|---|---|---|
| ingredient or active-ingredient combination | 5% | 8% |
| talcum | 95% | — |
| kaolin | — | 92% |

Dusts ready for use are obtained by mixing the active ingredient with the carrier, and grinding the mixture in a suitable mill.

| 8. Extruder granulate | |
|---|---|
| active ingredient or active-ingredient combination | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded, granulated and subsequently dried in a stream of air.

| 9. Coated granules | |
|---|---|
| active ingredient or active-ingredient combination | 3% |
| polyethylene glycol (MG 200) | 3% |
| kaolin | 94% |

The finely ground active ingredient or the active-ingredient combination is evenly applied, in a mixer, to the kaolin moistened with polyethylene glycol. Dust-free coated granules are obtained in this manner.

| 10. Suspension concentrate | |
|---|---|
| active ingredient or active-ingredient combination | 40% |
| ethylene glycol | 10% |
| nonylphenol-polyethylene glycol (15 mols of ethylehe oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active-ingredient combination is intimately mixed with the additives. There is thus obtained a suspension concentrate from which can be prepared, by dilution with water, suspensions of the concentration required.

EXAMPLE 1

Production of the starting compound: 3-chloro-4-[3-chloro-5-(1'-difluoro-2'-dichlorofluoroethyl)-2-pyridyloxy]-aniline 1.3 g of powdered potassium hydroxide are mixed together with 10 ml of dimethylsulfoxide. After the addition of 2.95 g of 2-chloro-4-nitrophenol, the mixture is stirred for 1 hour at 100° C., and is then cooled to 50° C. There are subsequently added dropwise 5.1 g of 2,3-dichloro-5-(1'-difluoro-2'-dichlorofluoroethyl)-pyridine dissolved in 5 ml of dimethyl sulfoxide, and the mixture is stirred at 120° C. for 5 hours in a nitrogen atmosphere. The reaction mixture is poured into ice water, and is extracted with toluene; the toluene phase is separated, washed with water, dried and concentrated by evaporation. 3-Chloro-4-[3-chloro-5-(1'-difluoro-2'-dichlorofluoroethyl)-2-pyridyloxy]-nitrobenzene is thus obtained in the form of white powder, m.p. 76°–78° C.

5.6 g of 3-chloro-4-[3-chloro-5-(1'-difluoro-2'-dichlorofluoroethyl)-2-pyridyloxy]-nitrobenzene are mixed together with 15 ml of concentrated hydrochloric acid. There are then added dropwise, at 70°–75° C., 13.1 g of tin dichloride ($SnCl_2.2H_2O$) in 20 ml of concentrated hydrochloric acid, and the reaction mixture is stirred at about 100° C. for 4 hours. It is poured onto ice, rendered alkaline with sodium hydroxide solution (50% by weight of NaOH), and extracted with dichloromethane; the extract obtained is washed until neutral, dried, highly concentrated by evaporation and filtered through silica gel. The resulting filtrate is concentrated by evaporation to thus obtain 3-chloro-4-[3-chloro-5'-(1'-difluoro-2'-dichlorofluoroethyl)-2-pyridyloxy]-aniline as yellow oil, $n_{21}{}^D = 1.5729$. The following starting compounds of the formula II are produced in an analogous manner:

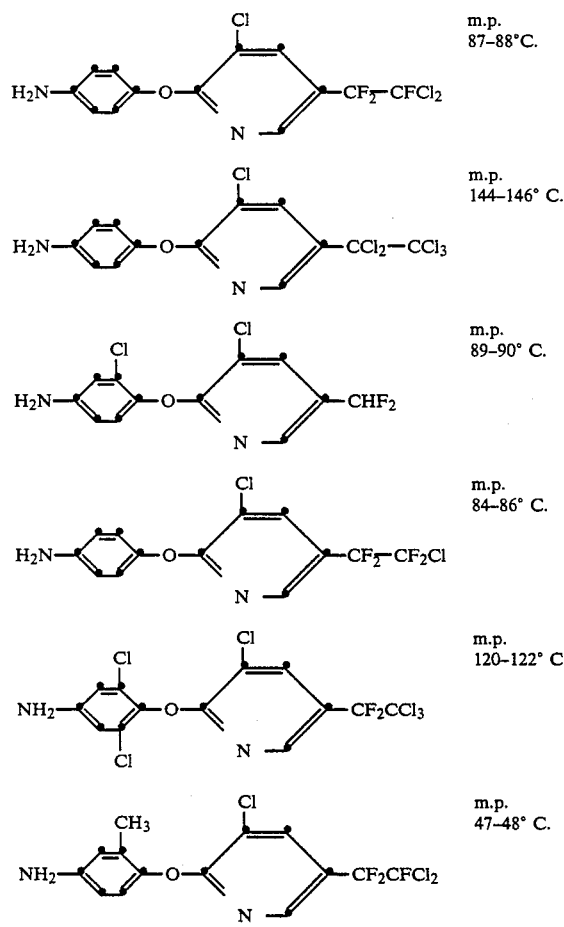

Production of $N^1$-3-chloro-4-[3-chloro-5-(1'-difluoro-2'-dichlorofluoroethyl)-2-pyridyloxy]-phenyl-$N^2$-2-chlorobenzoylurea 2.25 g of the resulting 3-chloro-4-[3-chloro-5-(1'-difluoro-2'-dichlorofluoroethyl)-2-pyridyloxy]-aniline are dissolved in 20 ml of absolute toluene; and there is then added dropwise, with the exclusion of moisture, 1 g of 2-chlorobenzoylisocyanate dissolved in 10 ml of toluene. The exothermic reaction is allowed to subside; and the crystalline precipitate which is formed after some time is filtered off with suction, washed with a small amount of hexane and dried. There is thus obtained $N^1$-3-chloro-4-[3-chloro-5-(1'-difluoro-2'-dichlorofluoroethyl)-2-pyridyloxy]-phenyl-$N^2$-2-chlorobenzoylurea, m.p. 225°–227° C. (compound No. 1).

The following compounds of the formula I are produced by a procedure analogous to that described in the foregoing:

| Comp. No. | $R_1$ | $R_2$ | $R_3$ | $R_4$ | $R_5$ | $R_6$ | Melting point [°C.] |
|---|---|---|---|---|---|---|---|
| 1 | Cl | H | Cl | H | —$CF_2$—$CFCl_2$ | Cl | 225–227 |
| 2 | F | F | H | H | —$CF_2$—$CFCl_2$ | Cl | 198–200 |
| 3 | Cl | H | H | H | —$CF_2$—$CFCl_2$ | Cl | 186–188 |
| 4 | F | F | Cl | H | —$CF_2$—$CFCl_2$ | Cl | 203–205 |
| 5 | F | F | H | H | —$CCl_2$—$CCl_3$ | Cl | 229–231 |
| 6 | F | F | H | H | —$CHF_2$ | Cl | 170–172 |
| 7 | F | F | Cl | H | —$CHF_2$ | Cl | 219–222 |
| 8 | F | F | H | H | —$CF_2$—$CF_2Cl$ | Cl | 188–190 |
| 9 | Cl | H | H | H | —$CF_2$—$CF_2Cl$ | Cl | 191–193 |
| 10 | F | F | Cl | Cl | —$CF_2$—$CF_2Cl$ | Cl | 227–229 |
| 11 | Cl | H | Cl | Cl | —$CF_2$—$CF_2Cl$ | Cl | 211–213 |
| 12 | F | F | Cl | Cl | —$CF_2$—$CCl_3$ | Cl | 234–236 |
| 13 | F | F | Cl | Cl | $CF_2$—$CFCl_2$ | Cl | 231–233 |
| 14 | Cl | H | Cl | Cl | $CF_2$—$CFCl_2$ | Cl | 220–222 |
| 15 | Br | H | Cl | Cl | $CF_2$—$CCl_3$ | Cl | 221–223 |
| 16 | $CH_3$ | H | Cl | Cl | $CF_2$—$CCl_3$ | Cl | 236–238 |
| 17 | F | F | $CH_3$ | H | $CF_2$—$CFCl_2$ | Cl | 190–192 |
| 18 | Cl | H | $CH_3$ | H | $CF_2$—$CF_2Cl$ | Cl | 195–196 |
| 19 | H | H | Cl | Cl | $CF_2$—$CF_2Cl$ | Cl | >240 |

There are produced by a procedure corresponding to that described in the foregoing also the following compounds of the formula I:

| Comp. No. | $R_1$ | $R_2$ | $R_3$ | $R_4$ | $R_5$ | $R_6$ |
|---|---|---|---|---|---|---|
| 20 | Cl | H | H | H | —$CCl_2$—$CCl_3$ | Cl |
| 21 | F | Cl | Cl | Cl | —$CF_2$—$CFCl_2$ | Cl |
| 22 | $CH_3$ | H | Cl | Cl | —$CF_2$—$CFCl_2$ | Cl |
| 23 | F | F | Cl | Cl | —$CF_2$—$CH_3$ | Cl |
| 24 | Cl | H | Cl | Cl | —$CF_2$—$CH_3$ | Cl |
| 25 | F | Cl | Cl | Cl | —$CF_2$—$CH_3$ | Cl |
| 26 | F | F | Cl | Cl | —$CF_2$—$CF_3$ | Cl |
| 27 | Cl | H | Cl | Cl | —$CF_2$—$CF_3$ | Cl |
| 28 | F | Cl | Cl | Cl | —$CF_2$—$CF_3$ | Cl |
| 29 | F | F | Cl | Cl | —$CCl_2$—$CH_3$ | Cl |
| 30 | Cl | H | Cl | Cl | —$CCl_2$—$CH_3$ | Cl |
| 31 | F | Cl | Cl | Cl | —$CCl_2$—$CH_3$ | Cl |
| 32 | F | F | Br | Br | —$CF_2$—$CHFCl$ | Cl |
| 33 | Cl | H | Br | Br | —$CF_2$—$CHFCl$ | Cl |
| 34 | F | F | Cl | H | —$CCl_2$—$CCl_3$ | Cl |
| 35 | Cl | H | Cl | H | —$CCl_2$—$CCl_3$ | Cl |
| 36 | F | F | Cl | Cl | —$CF_2$—$CFCl_2$ | F |
| 37 | F | F | Cl | Cl | —$CF_2$—$CFCl_2$ | Br |
| 38 | H | H | Cl | Cl | —$CF_2$—$CFCl_2$ | Cl |
| 39 | Br | Br | Cl | Cl | —$CF_2$—$CFCl_2$ | Cl |
| 40 | $CH_3$ | $CH_3$ | Cl | Cl | —$CF_2$—$CFCl_2$ | Cl |
| 41 | F | F | F | F | —$CF_2$—$CFCl_2$ | Cl |

EXAMPLE 2

Action against *Musca domestica*

50 g of freshly prepared CSMA nutrient medium for maggots are weighed off into each of a series of beakers. A specific amount of a 1% (by weight) acetonic solution of the respective active ingredient is transferred by pipette to the nutrient medium in each beaker. After a thorough mixing of the nutrient medium, the acetone is allowed to evaporate off for at least 20 hours. There are then deposited per active ingredient and concentration in each case 25 one-day-old *Musca domestica* maggots into each beaker containing the treated nutrient medium. After completion of pupation, the formed pupae are separated from the nutrient medium by flushing with water, and are placed into vessels closed with perforated lids. The pupae flushed out per batch are counted (toxic effect of the active ingredient on the development of the maggots), and after 10 days the number of flies which have emerged from the pupae is determined.

Compounds of the formula I according to Example 1 exhibit a good action in the above test.

EXAMPLE 3

Action against *Lucilia sericata*

1 ml of an aqueous preparation containing 0.5% of active ingredient is added to 9 ml of a culture medium at 50° C. About 30 freshly hatched *Lucilia sericata* maggots are then placed onto the culture medium, and after 48 and 96 hours, respectively, the insecticidal action is determined by ascertaining the mortality rate.

Compounds of the formula I according to Example 1 exhibit a good action in this test against *Lucilia sericata*.

EXAMPLE 4

Action against *Aedes aegypti*

Sufficient of a 0.1% acetonic solution of the respective active ingredient is transferred by pipette to the surface of 150 ml of water in a container to obtain a concentration of 12.5 ppm. After the acetone has evaporated off, 30–40 two-day-old Aëdes larvae are placed into the container. The mortality rate is ascertained after 2 days and after 7 days.

EXAMPLE 5

Insecticidal stomach-poison action

Cotton plants (about 20 cm in height) are sprayed with aqueous active-ingredient emulsions (obtained from a 10% emulsifiable concentrate), the active-ingredient emulsions containing 0.75, 3.0, 12.5, 50, 100 and 400 ppm, respectively, of the compound to be tested. After drying of the applied coating, larvae of *Spodoptera littoralis* in the $L_3$-stage and of *Heliothis virescens* in the $L_3$-stage, respectively, are settled onto the cotton plants. The test is carried out at 24° C. with 60% relative humidity. At intervals in each case of 24 hours, an assessment is made of the mortality rate and also of development and sheeding disturbances suffered by the deposited larvae.

EXAMPLE 6

Action on *Spodoptera litteralis* and *Heliothis virescens* (larvae and eggs)

Three cotton plants about 15–20 cm in height and grown in pots are treated with a sprayable liquid preparation of the respective active ingredient to be tested. After the drying of the applied coating, the potted plants are placed into a tin container of about 20 liters capacity, which is covered with a glass plate. The humidity inside the covered container is controlled in a manner ensuring that no condensation water is formed, and direct light falling onto the plants is avoided. The three plants are then infested in all as follows:

(a) 50 larvae of *Spodoptera littoralis* and *Heliothis virescens*, respectively, of the first larval stage;

(b) 20 larvae of *Spodoptera littoralis* and *Heliothis virescens*, respectively, of the third larval stage, and (c) two coatings of eggs of *Spodoptera littoralis* and *Heliothis virescens*, respectively (for this purpose, 2 leaves of a plant are in each case enclosed in a plexiglass cylinder sealed at each end with gauze); two coatings of eggs of Spodoptera, or a portion of a cotton-plant leaf on which are deposited eggs of Heliothis, are added to the enclosed leaves.

An evaluation, using untreated control plants as a comparison, is made after 4 and 5 days on the basis of the following criteria:

(a) number of living larvae, (b) inhibition of larval development and shedding, (c) damage caused by eating (scraping and hole damage), (d) hatching rate (number of larvae which have emerged from the eggs).

Compounds of the formula I according to Example 1 exhibit a good overall effectiveness in the above test.

EXAMPLE 7

Ovicidal action against *Spodoptera littoralis*

Eggs of *Spodoptera littoralis* deposited on filter paper are cut out of the paper and immersed in a 0.05% (by weight) solution of the active ingredient in an acetone/water mixture (1:1). The deposited eggs treated in this manner are then removed from this mixture, and placed at 28° C. with 60% relative humidity into plastics dishes. An assessment is made after 5 days of the hatching rate, that is, of the number of larvae which have developed from the treated eggs.

Compounds of the formula I according to Example 1 exhibit a good action in the above test.

EXAMPLE 8

Ovicidal action on *Epilachna varivestis*

20% by weight of active ingredient, 70% by weight of xylene and 10% by weight of a mixture of a reaction product of an alkylphenol with ethylene oxide and calcium dodecylbenzenesulfonate are mixed together, and from this concentrate are produced aqueous emulsions containing 800 ppm and 1600 ppm, respectively, of active ingredient.

In each case about 100 eggs of *Epilachna varivestis* (Mexican bean beetle), freshly deposited on *Phaseolus vulgaris* leaves, are moistened with the aqueous emulsions described above (concentrations 800 ppm and 1600 ppm, respectively, of active ingredient), and slightly dried. The treated clusters of eggs are kept in a ventilated vessel until the simultaneously deposited but untreated control eggs have hatched. An evaluation is made under a binocular microscope with regard to the percentage mortality rate achieved.

Compounds of the formula I according to Example 1 exhibit a good action in the above test.

EXAMPLE 9

Ovicidal action on *Heliothis virescens* and *Leptinotarsa decemlineata*

Corresponding proportions of a wettable pulverulent formulation containing 25% by weight of the active ingredient to be tested are mixed with specific amounts of water to give aqueous emulsions of increasing concentration of active ingredient. One-day-old clusters of eggs of Heliothis deposited on cellophane ® and of Leptinotarsa deposited on potato leaves are immersed for three minutes in the above respective emulsions containing the active ingredient to be tested, and are then filtered by suction on round filters. The egg clusters treated in this manner are subsequently laid out in Petri dishes and kept in darkness. After 6 to 8 days, the hatching rate compared with that of untreated control clusters is determined. The criterion for the evaluation is the minimum concentration of active ingredient required to effect a 100% destruction of the eggs.

Compounds of the formula I according to Example 1 exhibit a good action in the above test.

EXAMPLE 10

Action on *Laspeyresia pomonella* (eggs)

Deposited *Laspeyresia pomonella* eggs, not more than 24 hours old, are immersed on filter paper for 1 minute in an acetonic/aqueous solution containing 400 ppm of the active ingredient to be tested. After the drying of the solution on the eggs, they are laid out in Petri dishes and kept at a temperature of 28° C. The percentage hatching rate from the treated eggs is evaluated after six days.

Compounds of the formula I according to Example 1 exhibit a good action in the above test.

EXAMPLE 11

Effect on reproduction of *Anthonomus grandis*

Adult *Anthonomus grandis*, which have been hatched no longer than 24 hours, are transferred, in groups each of 25 beetles, to cages having lattice walls. The cages containing the bettles are then immersed for 5 to 10 seconds in an acetonic solution containing the active ingredient to be tested. After the bettles are again dry, they are placed, for copulation and oviposition, into covered dishes containing feed. Deposited eggs are flushed out with running water two to three times weekly; they are counted, disinfected by being placed for two to three hours into an aqueous disinfectant, and then deposited into dishes containing a suitable larval diet. An examination is made after 7 days to determine whether larvae have developed from the deposited eggs.

In order to ascertain the duration of the reproduction-influencing effect of the active ingredients tested, the oviposition of the beetles is observed during a period of about four weeks. The evaluation is on the basis of the reduction in the number of eggs laid and larvae hatched in comparison with that in the case of untreated control specimens.

EXAMPLE 12

Action against *Anthonomus grandis* (adults)

Two potted cotton plants in the 6-leaf stage are sprayed with aqueous emulsion preparations capable of wetting and containing 12.5, 50 and 100 ppm, respectively, of the active ingredient to be tested. After the drying of the applied coating (about 1.5 hours), 10 adult beetles (*Anthonomus grandis*) are settled onto each plant. A plastics cylinder, the upper opening of which is covered with gauze, is placed over each treated plant infested with the test insects, in order to prevent the beetles from escaping. The treated plants are kept at 25° C. with about 60% relative humidity. An evaluation is made after 2, 3, 4 and 5 days with respect to the percentage mortality rate suffered by the test beetles (% dorsal position), and also with respect to the antifeeding effect, in each case compared with that occurring with untreated control groups.

Compounds of the formula I according to Example 1 exhibit a good reproduction-reducing action in the above test.

Biological results

The following Table shows the results of biological tests on compounds according to the invention on the basis of the above biological Examples. The criterion used for evaluating the results of the tests was the % morality rate, the evaluation index being as follows:

A: 80–100% mortality rate at a concentration of 0.75 ppm of the compound tested;
B: 80–100% mortality rate at a concentration of 3.0 ppm of the compound tested;
C: 80–100% mortality rate at a concentration of 12.5 ppm of the compound tested;
D: 80–100% mortality rate at a concentration of 50 ppm of the compound tested;
E: 80–100% mortality rate at a concentration of 100 ppm of the compound tested; and
F: 80–100% mortality rate at a concentration of 400 ppm of the compound tested.

|  | Pesticidal effectiveness | | | |
|---|---|---|---|---|
| Comp. No. | Aedes larvae (Example 4) | Spodoptera larvae (Example 5) | Heliothis larvae (Example 5) | Anthonomus (Example 11) |
| 1 | — | D | D | — |
| 2 | C | A | B | — |
| 3 | C | C | E | — |
| 4 | C | B | B | — |
| 5 | C | D | E | — |
| 6 | C | F | — | — |
| 7 | — | D | — | D |
| 8 | — | B | C | C |
| 9 | — | C | D | E |
| 10 | — | C | D | E |
| 11 | — | C | C | E |
| 12 | — | E | E | — |

What is claimed is:

1. A compound of the formula

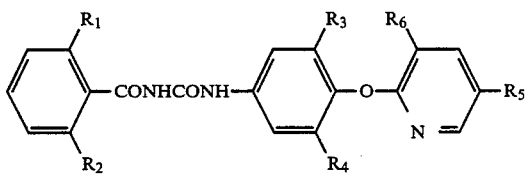

wherein
each of $R_1$, $R_2$, $R_3$ and $R_4$ is independently selected from the group consisting of hydrogen, methyl, fluoro, chloro or bromo;
$R_5$ is a chlorinated ethyl substituent selected from the group consisting of 2-chloro-1,1,2,2-tetrafluoroethyl; 2,2-dichloro-1,1,2-trifluoroethyl; pentachloroethyl; 1,1-difluoro-2,2,2-trichloroethyl; 1,1-dichloroethyl; 2-chloroethyl; 2,2-dichloroethyl; and 2,2,2-trichloroethyl; and
$R_6$ is fluoro, chloro or bromo.

2. A compound according to claim 1 wherein each of R₃ and R₄ is independently selected from the group consisting of hydrogen, methyl or chloro.

3. A compound according to claim 2 wherein R₆ is chloro.

4. A compound of the formula

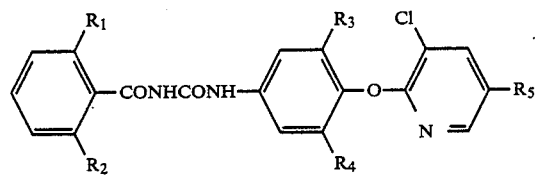

wherein
each of $R_1$ and $R_2$ is independently selected from the group consisting of hydrogen, methyl, fluoro, chloro and bromo;
each of $R_3$ and $R_4$ is independently selected from the group consisting of hydrogen, methyl or chloro; and
$R_5$ is $-CF_2CF_2Cl$, $-CF_2CFCl_2$, or $-CCl_2CCl_3$.

5. The compound according to claim 4 having the formula

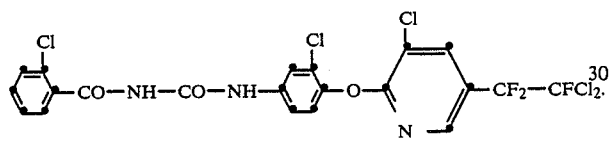

6. The compound according to claim 4 having the formula

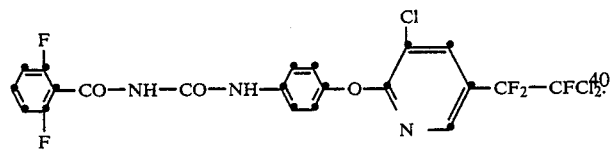

7. The compound according to claim 4 having the formula

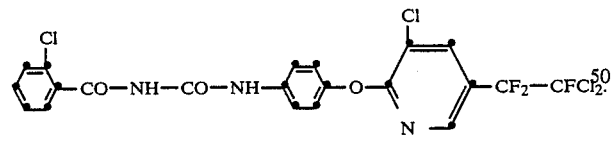

8. The compound according to claim 4 having the formula

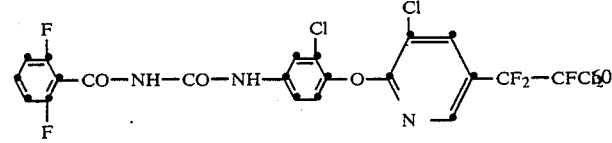

9. The compound according to claim 4 having the formula

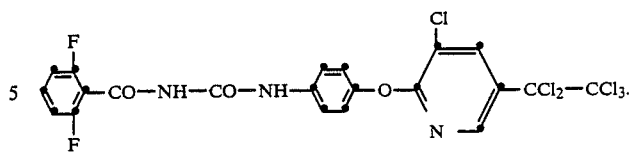

10. The compound according to claim 4 having the formula

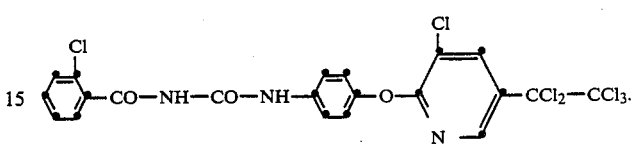

11. The compound according to claim 4 having the formula

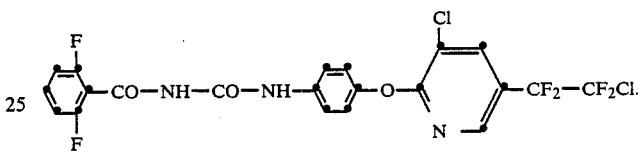

12. The compound according to claim 4 having the formula

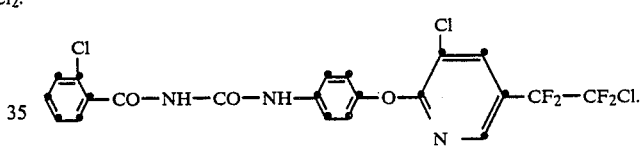

13. The compound according to claim 4 having the formula

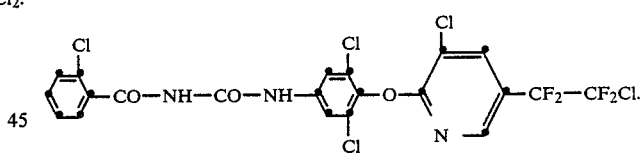

14. The compound according to claim 4 having the formula

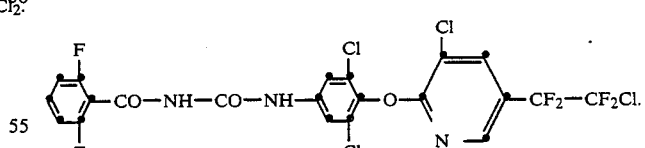

15. An insecticidal and acaricidal composition comprising an effective amount of a compound according to claim 1 and a carrier therefor.

16. The method of combating insects and members of the order Acarina which comprises applying to them or to their locus an effective amount of a compound according to claim 1.

* * * * *